United States Patent [19]

Takekawa

[11] 4,373,931
[45] Feb. 15, 1983

[54] METHOD OF MEASURING AGGLUTINATING REACTION AND A REACTION VESSEL THEREFOR

[75] Inventor: Hiroshi Takekawa, Kunitachi, Japan

[73] Assignee: Olympus Optical Company Limited, Tokyo, Japan

[21] Appl. No.: 193,625

[22] Filed: Oct. 3, 1980

[30] Foreign Application Priority Data

Oct. 9, 1979 [JP] Japan .................. 54-130280

[51] Int. Cl.³ .................. G01N 31/02; G01N 1/10; G01N 35/00
[52] U.S. Cl. .................. 436/539; 356/246; 422/72; 422/73; 422/102
[58] Field of Search .................. 23/230 B; 422/72, 73, 422/102; 356/246

[56] References Cited

U.S. PATENT DOCUMENTS

| | | | |
|---|---|---|---|
| 3,635,678 | 1/1972 | Seitz | 422/73 X |
| 3,869,214 | 3/1975 | Egli | 356/246 |
| 3,883,308 | 5/1975 | Matte | 422/64 |
| 4,148,607 | 4/1979 | Bernoco | 422/72 X |
| 4,278,437 | 7/1981 | Haggar | 422/73 X |
| 4,290,997 | 9/1981 | Suovaniemi | 422/102 X |
| 4,301,963 | 11/1981 | Nielsen | 422/102 X |
| 4,303,616 | 12/1981 | Kano | 422/102 X |

FOREIGN PATENT DOCUMENTS 1539674 9/1968 France .

*Primary Examiner*—Sidney Marantz
*Attorney, Agent, or Firm*—Stevens, Davis, Miller & Mosher

[57] ABSTRACT

Method for measuring agglutinating reaction by checking an agglutinates pattern caused by immunological agglutinating reaction while using a reaction vessel having at least one smooth recess formed on an inner sidewall surface thereof. After reaction liquid is placed therein, the reaction vessel is rotated about an axis thereof, so as to accelerate the agglutinating reaction by collecting corpuscles of the liquid in the recess. If the agglutinating reaction occurs, agglutinates released from the recess quickly sediment on the bottom of the reaction vessel to form an agglutinates pattern to be detected.

13 Claims, 19 Drawing Figures

FIG.1
PRIOR ART
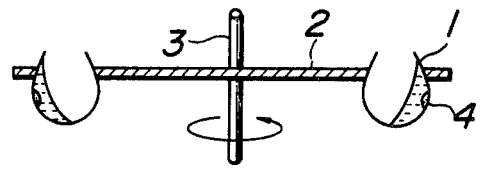
FIG.2
PRIOR ART
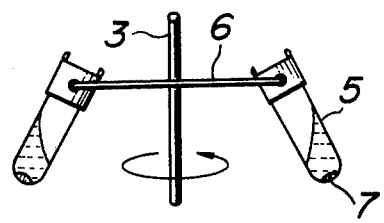
FIG.3A
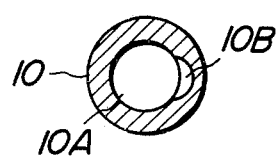
FIG.4A
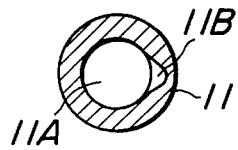
FIG.5A
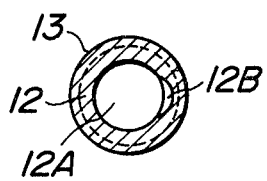
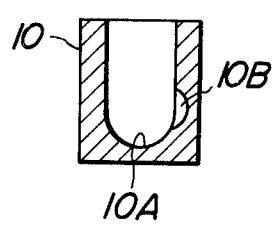
FIG.3B
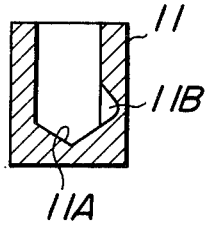
FIG.4B
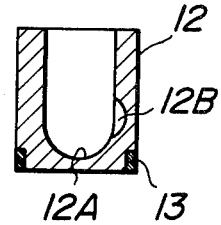
FIG.5B

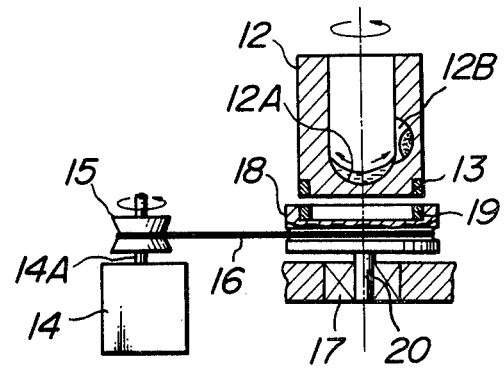
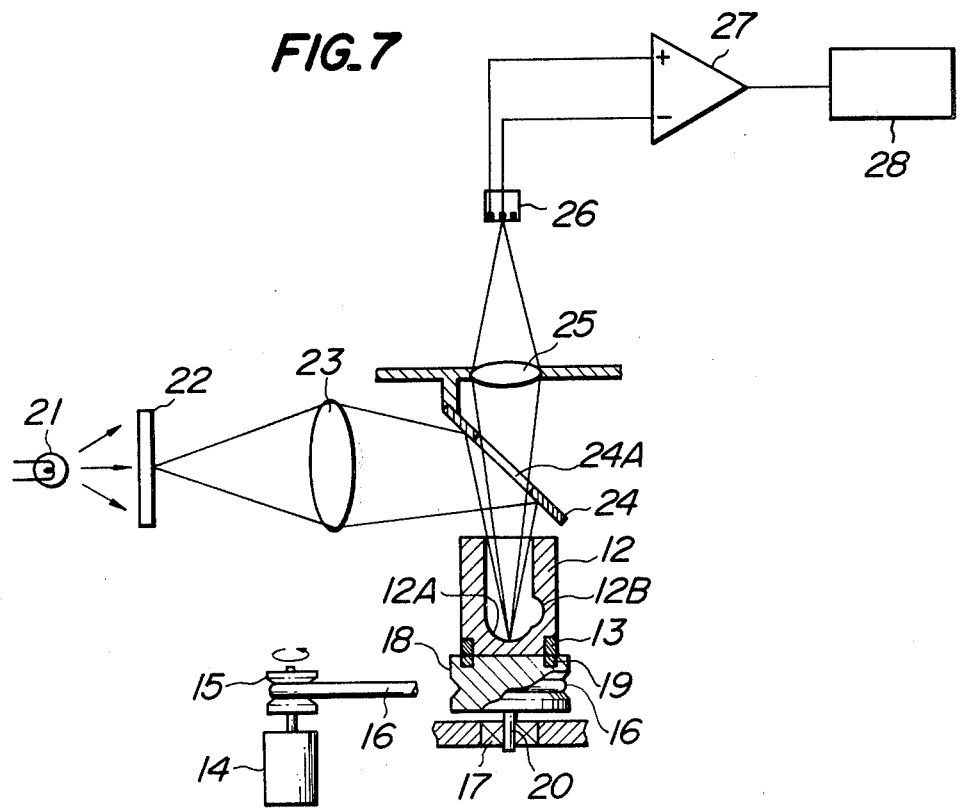

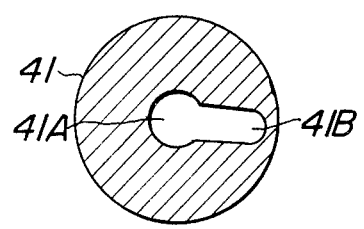
FIG_12A
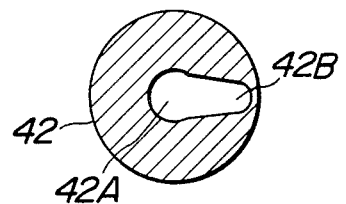
FIG_13A
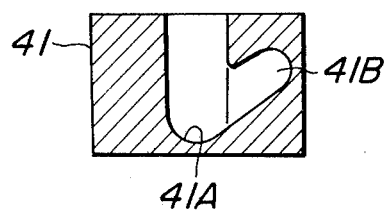
FIG_12B
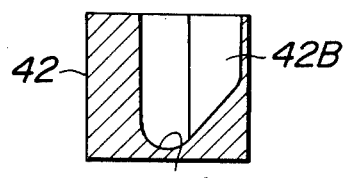
FIG_13B
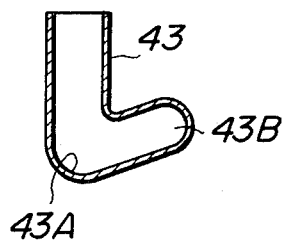
FIG_14

METHOD OF MEASURING AGGLUTINATING REACTION AND A REACTION VESSEL THEREFOR

BACKGROUND OF THE INVENTION

1. Field of the Invention

This invention relates to a method of measuring agglutinating reaction by checking an aggultinates pattern caused by immunological agglutinating reaction, and more particularly to a method of measuring corpuscle-agglutinating reaction for determination of blood group and for detecting antibodies and antigens based on an agglutinating pattern of blood corpuscles.

2. Description of the Prior Art

As an example of the prior art method of determining blood group, the method disclosed by U.S. Pat. No. 3,883,308 granted to Claude Matte (to be referred to as "Matte", hereinafter) will be briefly reviewed as shown in FIG. 1. The method of Matte comprises steps of pouring certain amounts of a centrifugated suspension having 2 to 5% of blood corpuscles to be analyzed and a specific antiserum into a reaction vessel having a curved bottom of brandy glass shape, agitating the suspension and the antiserum, keeping the reaction vessel standstill, effecting centrifugation by rotating a holder carrying the reaction vessels about the axis of the holder, for instance at a revolving speed of about 1,000 rpm, applying a special high-speed shake-up to the reaction vessel so as to disperse the precipitated blood corpuscles, agitating the reaction vessel comparatively slowly so as to collect agglutinates at the central portion of the bottom of the reaction vessel for producing an agglutinates pattern at the bottom of the reaction vessel and detecting the agglutinates pattern by photometry. This method is based on a phenomenon that, after the aforementioned shake-up and comparatively slow agitation, agglutinates combined by the agglutination are quickly collected at the central portion of the reaction vessel while non-agglutinated particles are dispersed again in the suspension and not collected at the central portion of the reaction vessel, within a short period of time.

As shown in FIG. 2, there is another prior art method of measuring agglutinating reaction based on the aforementioned phenomenon, which method uses reaction vessels of test tube like shape and a centrifuge adapted to receive the reaction vessels for effecting centrifugal precipitation, so as to facilitate collection of blood corpuscles at the bottom of each of the reaction vessels. After the centrifugal precipitation, the reaction vessel is shaken up at a high speed for dispersing combined blood corpuscles, and then the agglutinates are collected at the bottom of the reaction vessel for producing an agglutinates pattern.

In each of the prior art methods of measurement, the centrifugal precipitation is applied for the purposes of accumulating corpuscles to reduce distances between adjacent corpuscles and to facilitate occurrence of the agglutinating reaction. In actual devices for carrying the aforementioned prior art methods, to ensure a high efficiency of measurement, it is necessary to effect the centrifugal precipitation on a plurality of reaction vessels at one time. On the other hand, to improve the reliability of the result of the measurement, it is necessary to carry out the measurement on different reaction vessels under identical conditions. To this end, the reaction vessels must be disposed on one circle around one center of rotation. Therefore, to treat a large number of reaction vessels at one time, a large centrifuge with a large diameter becomes necessary, and an increase in the size of the centrifuge becomes inevitable. However, at the place where such measurement of the agglutinating reaction is carried out, there are usually a number of other measuring or analyzing instruments installed, so that reduction of instruments or devices for such measurement of agglutinating reaction to the smallest possible size is desirable. To meet this need for size reduction, it has been practiced to dispose a large number of the reaction vessels in two or three circular rows, each row having a circle along which the reaction vessels are disposed. In this arrangement, however, the outer circular row generates a larger centrifugal force than that of the inner circular row, so that the uniformity of the centrifugal force is lost and the aggregation of corpuscles becomes uneven, resulting in a loss of uniformity of the agglutinating reactions leading to a possible large error in the measurement which is a major shortcoming of the prior art. Since the result of measurement on the immunological agglutinating reaction may affect the life of a patient, the possibility of the aforementioned error must be minimized by all means.

Besides, to improve the measuring efficiency and to prevent any human error from entering into the measurement, A photoelectric means for detecting the agglutinates pattern is desirable, but it is difficult in the prior art to detect the agglutinates pattern at the same position with that for the centrifugal precitation, i.e., the position of effecting the reaction, because the point where the reaction vessel stops after rotation for the centrifugal precipitation is uncertain. Thus, it has been necessary to transfer the reaction vessel from the position of centrifugal precipitation to another position for detecting the agglutinates pattern. Accordingly, another disadvantage is caused in that the measurement requires an additional step and additional man power for the transfer and extra floor spaces for separate centrifugation and detection of agglutinates pattern.

SUMMARY OF THE INVENTION

An object of the present invention is to obviate the aforementioned shortcomings of the prior art, by providing an improvement in a method of measuring agglutinating reaction, which improvement facilitates simultaneous measurements of a large number of reacting liquid samples in a limited space, achievement of an increased accuracy of measurement by uniformly effecting the agglutinating reaction, and fulfillment of the agglutinating reaction and the detection of the agglutinates pattern at one position.

According to the present invention, in measuring the agglutinating reaction through detection of the agglutinates pattern caused by immunological agglutinating reaction, a certain amount of reaction liquid is placed in a reaction vessel having at least one smooth recess formed on an inner sidewall surface thereof, and the reaction vessel carrying the reaction liquid is rotated about its own axis to accumulate corpuscles of the reaction liquid in the aforementioned recess for effecting agglutinating reaction at an accelerated rate, and then the corpuscles are released from the recess, whereby in the case of the presence of the agglutinating reaction, the agglutinated corpuscles quickly sediment on the bottom of the reaction vessel and generate an agglutinates pattern thereon, which agglutinates pattern is to be detected.

Furthermore, the present invention relates to a reaction vessel to be used in the aforementioned method of measuring agglutinating reaction. The reaction vessel of the invention is used in a method of measuring agglutinating reaction by placing reaction liquid whose agglutinating reaction is to be measured into the reaction vessel, rotating the reaction vessel about its own axis so as to accumulate corpuscles of the reaction liquid for accelerating the agglutinating reaction, and detecting an agglutinates pattern formed thereby, which reaction vessel is characterized by having at least one smooth recess formed on an inner sidewall surface thereof in such a manner that the corpuscles of the reaction liquid are accumulated in the recess during the aforementioned rotation of the reaction vessel about its own axis.

BRIEF DESCRIPTION OF THE DRAWINGS

For a better understanding of the invention, reference is made to the accompanying drawings, in which:

FIG. 1 is a diagrammatic illustration of a conventional method of measuring agglutinating reaction in which centrifugal precipitation is effected by using a reaction vessel having a brandy cup shaped bottom;

FIG. 2 is a diagrammatic illustration of a conventional method of measuring agglutinating reaction which uses reaction vessels of test tube like shape;

FIGS. 3A, 3B, 4A, 4B, 5A and 5B are horizontal and vertical sectional views showing three different reaction vessels according to the present invention, respectively;

FIG. 6 is a schematic view of the construction of an automatic driving mechanism for effecting the method of measuring agglutinating reaction of the invention, which mechanism uses the reaction vessel of FIG. 5;

FIG. 7 is a schematic view of the construction of a means for detecting an agglutinates pattern;

FIGS. 12A, 12B, 13A and 13B are horizontal and vertical sectional views of two other reaction vessels according to the present invention; and FIG. 14 shows a vertical sectional view of another reaction vessel according to the present invention.

Like parts are designated by like numerals and symbols throughout different views of the drawings.

DETAILED DESCRIPTION OF THE PREFERRED EMBODIMENTS

Figure 8:
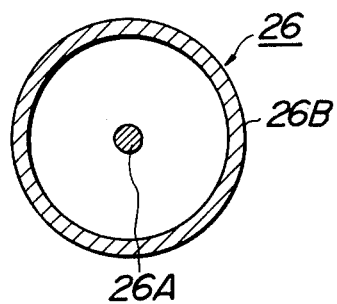
FIG. 8 is a schematic plan view showing the positions of photoelectric converting elements in the means of FIG. 7.

Referring to FIG. 1 schematically showing the method of Matte, reaction vessels 1 having bottoms of brandy glass shape are carried by a holder 2, which holder rotates about an axis 3, so as to generate agglutinates of blood corpuscles 4. In FIG. 2 showing another prior art method, reaction vessels 5 of test tube shape are mounted on a centrifuge 6, so that blood corpuscles 7 are collected at the bottom of each reaction vessel 5. The prior art methods as illustrated in FIGS. 1 and 2 have shortcomings as pointed out above herein.

FIGS. 3A and 3B show the construction of an embodiment of a reaction vessel according to the present invention. A reaction vessel 10 shown in the figure is cylindrically shaped and has a bottom 10A of substantially semi-spherical shape and a substantially semi-spherical side recess 10B formed on the inner sidewall surface thereof.

FIGS. 4A and 4B show a cylindrical reaction vessel 11, which is another embodiment of the reaction vessel according to the present invention. The reaction vessel 11 has a conical bottom portion 11A and a conical recess 11B formed on the inner sidewall surface thereof. It should be noted that the vertex of the conical recess 11B is rounded or chamfered, as shown in the figure.

FIGS. 5A and 5B illustrate still another embodiment of the reaction vessel according to the present invention. The reaction vessel 12 of this embodiment is cylindrically shaped with a substantially semi-spherical bottom 12A and a substantially semi-spherical recess 12B formed on the inner sidewall surface thereof, as in the case of the embodiment of FIGS. 3A and 3B. The reaction vessel 12 of FIG. 5 has a permanent magnet ring 13 embedded at the bottom portion thereof.

In the present invention, a certain amount of reaction liquid is placed in the reaction vessel, i.e., one of the illustrated vessels 10, 11, or 12 having a smooth sidewall recess 10B, 11B, or 12B, so that as the reaction vessel is rotated about its own axis, corpuscles of the reaction liquid are accumulated in the sidewall recess to accelerate the agglutinating reaction.

FIG. 6 shows an example of driving mechanisms for rotating individual reaction vessels about their own axes, respectively. The example of FIG. 6 uses the reaction vessels 12 shown in FIGS. 5A and 5B. A driving motor 14 carries a pulley 15 secured to an output shaft 14A thereof. An endless belt 16 extends between the pulley 15 on the driving motor 14 and another pulley 18 rotatably supported by an axis 20 mounted on a bearing 17. The pulley 18 carries a permanent magnet ring 19 integrally secured to the top surface thereof, so that the permanent magnet ring 19 magnetically attracts the permanent magnet ring 13 embedded at the bottom of the reaction vessel 12. As a result, the reaction vessel 12 carrying the reaction liquid is replaceably secured to the top of the pulley 18 by the magnetic attraction between the two permanent magnet rings 13 and 19. Thus, the reaction vessel 12 can be rotated about its own axis 20 by revolving the pulley 18 by the driving motor 14 through the endless belt 16. When the inside diameter of the reaction vessel 12 is 10 to 20 mm, the preferable range of its revolving speed about its own axis 20 is 5,000 to 10,000 rpm.

When the reaction vessel 12 is rotated at a high speed as mentioned above, the reaction liquid held at the bottom 12A of the reaction vessel 12 is forced away from the axis of rotation 20 toward the sidewall thereof by the centrifugal force caused by the rotation, as shown by the arrows of FIG. 6. Since the sidewall has the sidewall recess 12B formed thereon, the reaction liquid in the proximity of the recess 12B tends to move thereto. Due to the viscosity of the reaction liquid, the movement of the reaction liquid in the vicinity of the recess 12B toward the recess 12B acts to pull the remainder of the reaction liquid into the recess 12B. Corpuscles of the reaction liquid, such as blood corpuscles, are accumulated at the bottom portion or farthest portion from the axis 20 of the recess 12B due the centrifugal force, and the distances between adjacent corpuscles are so reduced that the agglutinating reaction is accelerated. When the rotation about the axis 20 ceases, the reaction liquid returns from the recess 12B to the bottom 12A of the reaction vessel 12 by gravity. During this return travel, the reaction liquid is agitated, and the corpuscles are dispersed. Accordingly, in the case of absence of the agglutinating reaction, the corpuscles are suspended again in the reaction liquid, so that no agglutinates pattern is formed on the bottom 12A of the reaction vessel 12. On the other hand, in the case of presence of the agglutinating reaction, the aforementioned agitation during the return of the reaction liquid toward the bottom 12A does not disperse agglutinates formed by the agglutination, and the agglutinates quickly sediment on the bottom 12A of the reaction vessel 12 and the sediments are collected thereon so as to generate an agglutinates pattern at the central portion of the bottom 12A. The agglutinates pattern can be detected by a photoelectric means.

FIG. 7 illustrates an example of the photoelectric means for detecting the agglutinates pattern. In the present invention, the reaction vessel 12 is rotated only about its own axis 20, so that the reaction vessel 12 is not displaced on a plane perpendicular to the axis 20. Thus, the detection of the agglutinates pattern can be carried out at the same location as that for effecting the agglutinating reaction. Therefore, the present invention is advantageous in that two shortcomings of the prior art are eliminated; namely, the man power necessary for moving the reaction vessel from a location for effecting the agglutinating reaction to a location for detecting the agglutinates pattern is eliminated, and the overall size of an instrument for carrying out the detection of the agglutinating reaction can be reduced. In the example of FIG. 7, the agglutinates pattern formed in the reaction vessel is detected from above by means of a reflection type optical system. To this end, light emanating from a light source 21 is passed through a diffusion plate 22 for making the brightness thereof uniform. The light from the diffusion plate 22 is directed to the bottom 12A of the reaction vessel 12 through a lens 23 and a reflective mirror 24 with a hole 24A, so as to illuminate the bottom 12A. The light reflected from the bottom 12A is directed to another lens 25 through the hole 24A of the mirror 24 so as to produce an image of the bottom 12A on a photoelectric converter element assembly 26. Referring to FIG. 8, the photoelectric converter element assembly 26 has a central member 26A for receiving the light of an image of the central portion of the bottom 12A and a peripheral member 26B for receiving the light of an image of the peripheral portion of the bottom 12A. The output signals from the two members 26A and 26B are applied to a differential amplifier 27, to produce a difference signal representing the difference between the two output signals, which difference signal is applied to a decision circuit 28 so as to determine presence or absence of the agglutinating reaction and/or the degree of agglutination. More particularly, when the agglutinating reaction does not occur, the amount of the light incident to the member 26A is substantially the same as that of the light incident to the member 26B, and the output signal or the difference signal from the differential amplifier 27 is zero or extremely small. On the other hand, when the agglutinating reaction occurs, the agglutinates are collected at the central portion of the bottom 12A of the reaction vessel 12, so that the amount of the light incident to the member 26A becomes smaller than that of the light incident to the member 26B, and the output voltage or the difference signal from the differential amplifier 27 becomes very large.

Figure 9:
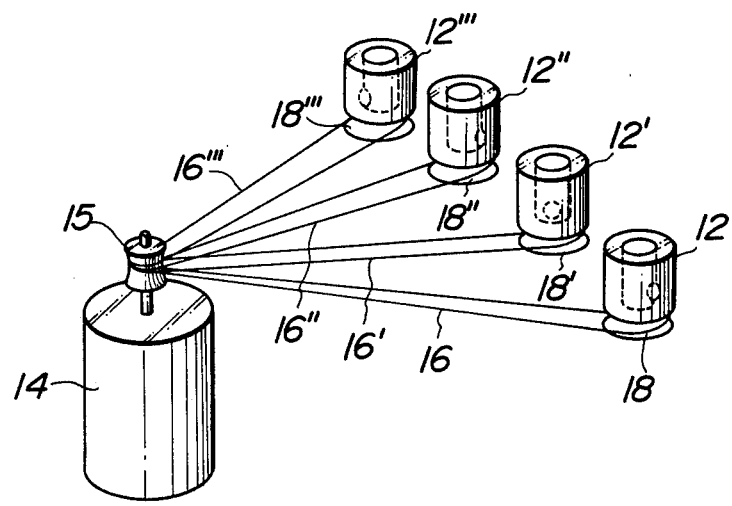
FIG. 9 is a schematic perspective view showing the manner in which a number of reaction vessels are rotated about their own axes, respectively, by the driving mechanism of FIG. 6.

FIG. 9 schematically illustrates an apparatus for rotating a plurality of individual reaction vessels about their axes, respectively, by using the automatic driving mechanism of FIG. 6. A plurality of endless belts 16, 16', 16", . . . operatively engage the pulley 15 connected to the driving motor 14, and the opposite end of each of the endless belts operatively engages a corresponding one of the pulleys 18, 18', 18", . . . carrying the reaction vessels 12, 12', 12", . . . respectively. With this disposition, a plurality of the reaction vessels can be simultaneously rotated by the one motor 14, while causing each vessel to rotate its own axis, so that centrifugal force applied to the reaction liquids in different reaction vessels are the same with each other, so as to improve the accuracy of the measurement.

Figure 10:
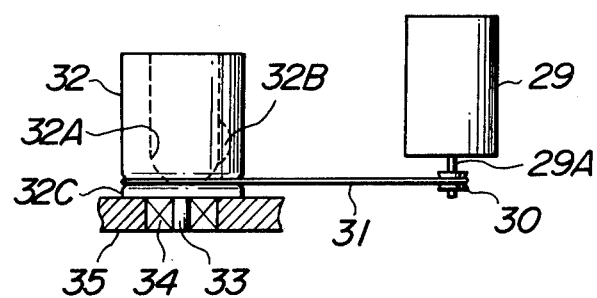
FIGS. 10 and 11 are schematic views of other examples of the mechanism to cause each reaction vessel to rotate about its own axis.

FIG. 10 schematically shows another embodiment of the reaction vessel of present invention and an automatic driving mechanism therefor. In the embodiment of FIG. 10, a driving motor 29 has an output shaft 29A with a pulley 30 secured thereto, and an endless belt 31 operatively engages the pulley 30. A reaction vessel 32 of this embodiment has a substantially semi-spherical bottom portion 32A and a substantially semi-spherical recess 32B formed on the inner sidewall surface thereof. An annular groove 32C with a V-shaped cross section is formed at the outer peripheral surface of the bottom portion of the reaction vessel 32. The opposite end of the endless belt 31 operatively engages the annular groove 32C. The reaction vessel 32 has a shaft 33 integrally secured to the outer bottom surface thereof, which shaft 33 is rotatably held by a bearing 34 secured to a holder 35. Thus, the reaction vessel 32 is rotated by the driving motor 29 through the endless belt 31.

Figure 11:
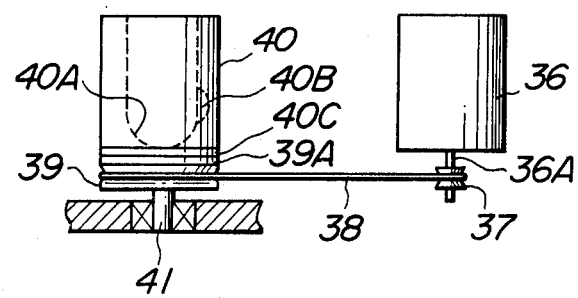

FIG. 11 diagrammatically illustrates another reaction vessel according to the present invention and an automatic driving mechanism therefor. Referring to the figure, the rotation of a driving motor 36 is transmitted to a rotatably-supported pulley 39, through a pulley 37 on the motor 36 and an endless belt 38 extending therebetween. The pulley 39 has a frictional disk 39A secured to the top surface thereof, which friction disk is made of felt, rubber, or like highly frictional material. A reaction vessel 40 of this embodiment has a substantially semi-spherical bottom portion 40A and a substantially semi-spherical recess 40B formed on the inner sidewall thereof. Another friction disk 40C is secured to the outer bottom surface of the reaction vessel 40, which friction disk 40C is also made of felt, rubber, or like highly frictional material. Accordingly, the frictional engagement between the frictional disks 39A and 40C allows the driving motor 36 to rotate the reaction vessel 40 about its own axis. In this case, to prevent the reaction vessel 40 from overturning, a suitable means may engage the outer peripheral surface of the reaction vessel 40 in a rotatable manner. For instance, three guide rollers may rotatably engage the outer peripheral surface of the reaction vessel 40 with angular displacements of 120° between adjacent guide rollers, each of which guide rollers is rotatable about its own axis parallel to the axis of the reaction vessel.

FIGS. 12A and 12B show a different form of the reaction vessel according to the present invention. A reaction vessel 41 of this embodiment has a substantially semispherical bottom 41A and a cylindrical recess 41B continuously extending upwardly along the inner sidewall surface from the bottom portion 41A at an angle to the bottom portion.

In another reaction vessel 42 according to the present invention, as shown in FIGS. 13A and 13B, a bottom portion 42A of the vessel 42 is semi-spherical and a recess 420 is formed on the inner sidewall surface of the vessel 42 so as to extend in the depth direction of the vessel with a bottom surface of the recess extending upwardly from the bottom portion 43A at an angle thereto. Thus, the recess 42B of this embodiment extends to the top of the reaction vessel 42 in parallel to the axis thereof, so that this embodiment is easy to manufacture.

FIG. 14 schematically shows a reaction vessel 43 of tubular shape, as another embodiment of the present invention. The lower end portion of the tubular reaction vessel 43 is bent so that the bent end portion extends upwardly at an angle to vertical, whereby a substantially semi-spherical bottom portion 43A an a recess 43B are formed.

In the reaction vessels illustrated in FIGS. 12 through 14, the inner bottom surface of the sidewall recess is slanted toward the inner bottom surface of the reaction vessel itself, so that when the high-speed rotation of the reaction vessel is completed, the reaction liquid can be easily collected at the bottom portion of the reaction vessel.

The present invention is not restricted to the aforementioned embodiments alone, and numerous modifications and changes are possible. For instance, the shape of the reaction vessel can be modified in various ways. More particularly, the bottom portion of the reaction vessel is not restricted to be substantially semi-spherically curved, but the shape of the bottom portion of the reaction vessel can be of inverse gable-roof shape, inverse shed-roof shape, inverse pyramid shape, or other suitable shape. Besides, the shape of the sidewall recess of reaction vessel is not restricted to that of the illustrated embodiments, but many other suitable shapes can be used therein. Moreover, the mechanism for rotating the reaction vessel about its own axis can be modified in many ways; for instance, a gear may be secured to a member rotatably holding the reaction vessel so that adjacent reaction vessels are operatively connected by the gears thus secured, for effecting the rotation of the individual reaction vessels about the axes of the individual reaction vessels respectively. In the present invention, the means for detecting the agglutinates pattern is not restricted to the photoelectric means, but the agglutinates pattern can be detected by bare eyes of laboratory technicians, and photoelectric detecting means of other types, such as perspective type photoelectric detective means, can be also used for achieving the object of the invention. If the perspective type photoelectric detective means is used, the reaction vessel must be made of transparent material and the holder of the reaction vessel must not interfere with the propagation of the light passing through the bottom portion of the reaction vessel.

What is claimed is:

1. In a method of measuring an agglutination reaction by detecting an agglutination pattern due to an immunological agglutination reaction, the improvement comprising the steps of introducing a reaction liquid containing corpuscles into a reaction vessel having a bottom and at least one recess formed in an inner sidewall thereof and smoothly communicated with the bottom;

rotating said reaction vessel about an axis thereof to collect at least a part of the reaction liquid in said recess for accelerating the agglutination reaction;

stopping the rotation of the reaction vessel to release the reaction liquid including agglutinated or non-agglutinated corpuscles from said recess into the bottom of the vessel due to gravity;

mixing the corpuscle-containing liquid with the reaction liquid contained in the bottom of the vessel so that, in case of agglutination, the agglutinated corpuscles settle on the bottom without being separated from each other, whereas in case of non-agglutination, the corpuscles are suspended in the reaction liquid; and detecting the agglutination pattern formed on the bottom by the settled corpuscles.

2. The method of claim 1, wherein a plurality of different reaction liquids are placed in corresponding reaction vessels and the reaction vessels are rotated simultaneously, each of said reaction vessels rotating about an axis passing therethrough.

3. The method of claim 1, wherein said reaction vessel has a substantially semi-spherical bottom surface.

4. The method of claim 1, wherein said recess is substantially semi-sphericallly shaped.

5. The method of claim 1, wherein said reaction vessel has a substantially conical bottom surface.

6. The method of claim 1, wherein said recess is substantially conically shaped with a rounded vertex.

7. The method of claim 1, wherein said reaction vessel has a permanent magnetic ring embedded at the bottom portion thereof.

8. A reaction vessel for measuring an agglutination reaction comprising:

a substantially tubular member comprising a cylindrical body having a side wall and a longitudinal axis;

an opening provided at an upper end of the cylindrical body;

a bottom wall having a generally concave inner bottom surface; and a recess formed in said side wall, said recess having an inner surface which extends from the inner surface of the side wall of the cylindrical body, said recess having a central axis which is substantially perpendicular to the longitudinal axis of the cylindrical body for facilitating gravity flow of fluid from said recess back to said inner bottom surface.

9. A reaction vessel as set forth in claim 8, wherein said reaction vessel has a substantially semi-spherical bottom surface.

10. A reaction vessel as set forth in claim 8, wherein said recess is substantially semi-spherically shaped.

11. A reaction vessel as set forth in claim 8, wherein said reaction vessel has a substantially conical bottom surface.

12. A reaction vessel as set forth in claim 8, wherein said recess is substantially conically shaped with a rounded vertex.

13. A reaction vessel as set forth in claim 8, wherein said reaction vessel has a permanent magnetic ring embedded at the bottom portion thereof.

* * * * *